United States Patent

Monkiewicz et al.

[11] Patent Number: 6,100,408
[45] Date of Patent: Aug. 8, 2000

[54] PROCESS FOR PREPARING 3-GLYCIDYLOXYPROPYLTRIALKOXYSILANES

[75] Inventors: Jaroslaw Monkiewicz, Rheinfelden; Stefan Bade, Haltern; Uwe Schoen, Rheinfelden, all of Germany

[73] Assignee: Huels Aktiengesellschaft, Marl, Germany

[21] Appl. No.: 09/246,953

[22] Filed: Feb. 9, 1999

[30] Foreign Application Priority Data

Feb. 9, 1998 [DE] Germany ............................ 198 05 083

[51] Int. Cl.⁷ ............................ C07F 7/08; C07D 303/02
[52] U.S. Cl. ............................................................ 549/215
[58] Field of Search ................................................ 549/215

[56] References Cited

U.S. PATENT DOCUMENTS

| | | | |
|---|---|---|---|
| 4,736,049 | 4/1988 | Suzuki et al. ............................ | 556/479 |
| 4,966,981 | 10/1990 | Takai et al. ............................... | 549/215 |
| 5,115,069 | 5/1992 | Motegi et al. ............................ | 528/15 |
| 5,420,323 | 5/1995 | Jung et al. ............................... | 556/415 |
| 5,583,194 | 12/1996 | Crivello et al. ........................... | 528/15 |

*Primary Examiner*—Paul F. Shaver
*Attorney, Agent, or Firm*—Oblon, Spivak, McClelland, Maier & Neustadt, P.C.

[57] ABSTRACT

The invention relates to a process for preparing 3-glycidyloxypropyltrialkoxysilanes of the general formula $$CH_2(O)CHCH_2-O-(CH_2)_3Si(OR)_3 \qquad (I),$$

in which R is an alkyl radical, by reacting allyl glycidyl ether $$CH_2(O)CHCH_2-O-CH_2CH=CH_2 \qquad (II),$$

with a trialkoxysilane of the general formula $$HSi(OR)_3 \qquad (III),$$

in which R is again an alkyl radical, in a heterogeneous, platinum-catalyzed hydrosilylation reaction, where the catalyst employed is a platinum(0) catalyst on a nonmetallic support.

18 Claims, No Drawings

PROCESS FOR PREPARING 3-GLYCIDYLOXYPROPYLTRIALKOXYSILANES

BACKGROUND OF THE INVENTION

1. Field of the Invention

The invention relates to a process for preparing 3-glycidyloxypropyltrialkoxysilanes from allyl glycidyl ethers and a trialkoxysilane via platinum-catalyzed hydrosilylation.

2. Description of the Background

3-Glycidyloxypropyltrialkoxysilanes represented by formula (I), shown below, are important industrial intermediates or end products in organosilane chemistry. They are used, inter alia, as adhesion promoters in connection with composite materials; for example, in the paints and glass fibers industry, in foundry engineering and in the adhesives industry. An important role is also played by the 3-glycidyloxypropyltrialkoxysilanes (I) in connection with the coating of optical glasses.

3-Glycidyloxypropyltrialkoxysilanes (I) are prepared by reacting a hydrogen-bearing trialkoxysilane (III) ("H-silane") with allyl glycidyl ether represented by formula (II), shown below, in a hydrosilylation reaction according to the equation $$CH_2(O)CHCH_2OCH_2CH=CH_2 + HSi(OR)_3 \rightarrow CH_2(O)CHCH_2O(CH_2)_3Si(OR)_3.$$

Here, R is an alkyl radical. When R is methyl, 3-glycidyloxypropyltrimethoxysilane ("GLYMO") is produced. When R is ethyl, 3-glycidyloxypropyltriethoxysilane ("GLYEO") is produced. Byproducts of this reaction include two isomers of (I):

$$CH_2(O)CHCH_2-O-CH_2CH[Si(OR)_3]CH_3 \quad (IV),$$

which is also referred to as iso-3-glycidyloxypropyltrialkoxysilane, and an eight-membered heterocyclic compound of the formula:

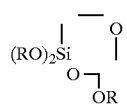

(V)

Additional byproducts are glycidyloxytrialkoxysilane, propyltrialkoxysilane, 1-methylvinyl glycidyl ether and tetraalkoxysilane, and also high-boiling components.

Hydrosilylation reactions of H-silanes with compounds containing a C=C double bond are conducted continuously or batchwise in the presence of a noble metal catalyst. 3-Glycidyloxypropyltrialkoxysilanes (I) are generally prepared in a homogeneous system using hexachloroplatinic (IV) acid as catalyst (see e.g. EP 0 277 023, EP 0 288 286, JP 128763 and DE 21 59 991). Disadvantages of the process with homogeneous catalysis are the difficulty of controlling the temperature during the reaction, the unavoidable task of separating off the catalyst, and the increased formation of byproducts as a result of secondary reactions of the target product under the influence of the homogeneously dissolved catalyst and/or as a consequence of unintended "outliers" in the temperature regime. Especially when catalyst is entrained into the distillative workup stage, the distillation is accompanied by the formation of the abovementioned isomers (IV) and (V) and of dimers and trimers of the 3-glycidyloxypropyltrialkoxysilanes (I). In addition, processes using hexachloroplatinic acid are not chlorine-free, which impairs the quality of the product and promotes, for example, the dissociation of trialkoxysilanes (II) into tetraalkoxysilanes.

EP 0 548 974 describes heterogeneous noble metal catalysts, namely rhodium and platinum, as metals or in the form of compounds which comprise metals as support material and can be used, inter alia, for the preparation of 3-glycidyloxypropyltrialkoxysilanes (I). Also described are noble metal complexes immobilized on nonmetallic supports, such systems likewise being employed for preparing 3-glycidyloxypropyltrialkoxysilanes (I) by hydrosilylation.

EP 0 262 642 describes rhodium-based catalysts for the preparation of 3-glycidyloxypropyltrialkoxysilanes (I), and indeed describes catalysts for both homogeneous and heterogeneous catalysis. The rhodium catalysts for homogeneous catalysis give yields of 3-glycidyloxypropyltrialkoxysilanes (I) of around 70%, while those for heterogeneous catalysis, comprising 5% rhodium on activated carbon as support, give yields of from 70 to 80%. The advantage of the rhodium catalysts over platinum catalysts is said to lie in the reduced sensitivity of the former toward nitrogen compounds, thereby raising the yield of 3-glycidyloxypropyltrialkoxysilanes (I) and reducing the loss of activity suffered by the catalysts.

U.S. Pat. No. 4,736,049 describes, quite generally, hydrosilylation reactions catalyzed homogeneously or heterogeneously with compounds of platinum or with metallic platinum and taking place in the presence of a carboxamide of the general formula $RCONR_1R_2$. In relation to supported catalysts mention is made only of platinum on charcoal. The presence of the carboxamide is said, in general terms, to favor the formation of the desired β adduct. According to EP 0 262 642, however, nitrogen compounds, for the specific case of the preparation of 3-glycidylpropyltrialkoxysilanes (I) using platinum catalysts, are said to lessen, quality and are therefore regarded as unfavorable.

SUMMARY OF THE INVENTION

One object of the invention is to provide an improved, extremely simple, heterogeneously catalyzed process for preparing 3-glycidyloxypropyltrialkoxysilanes (I).

This object is surprisingly achieved by a process for preparing 3-glycidyloxypropyltrialkoxysilanes of the general formula:

$$CH_2(O)CHCH_2-O-(CH_2)_3Si(OR)_3 \quad (I),$$

in which R is an alkyl radical, by reacting allyl glycidyl ether:

$$CH_2(O)CHCH_2-O-CH_2CH=CH_2 \quad (II),$$

with a trialkoxysilane of the general formula:

$$HSi(OR)_3 \quad (III)$$

in which R is again an alkyl radical, in a heterogeneous, platinum-catalyzed hydrosilylation reaction, where the catalyst is a platinum(0) catalyst on a nonmetallic support.

The process of the invention is associated with a series of surprising advantages:

In contradistinction to homogeneously catalyzed hydrosilyation, there are no losses of catalyst, the catalyst need not be introduced into the reaction by way of appropriate metering systems and need not be separated off from the reaction mixture.

Owing to the minimized formation of byproducts, the selectivity of the formation of 3-glycidylpropyltrialkoxysilanes (I) is >90%.

The catalyst and all components are free from chloride, thereby minimizing the dissociation of trialkoxysilanes (III) into tetraalkoxysilanes.

The temperature regime can be controlled readily, which contributes to optimizing the selectivity. At temperatures up to about 140° C., high-boiling linear byproducts and low-boiling cyclic byproducts are formed only in very small amounts.

The platinum need be present on the support only in very low concentrations of from 0.01 to 1% by mass.

Moreover, the price of platinum is much lower than that of rhodium.

The catalyst can be prepared in a simple manner by impregnating or spraying the support with a solution of a platinum (II) or platinum (IV) compound, drying the support thus treated, and then reducing the platinum (II) or platinum (IV) compound to Pt (0) in a hydrogen atmosphere.

The formation of the heterocyclic compound (V) is reliably prevented since no homogeneously dissolved catalyst is able to pass into the distillation stage.

Consequently, the reaction mixture is easier to separate, since there is no need to separate off any heterocyclic compound (V).

The isomerization of the allyl glycidyl ether (II) to the 1-methylvinyl glycidyl ether, which is favored in a homogeneous reaction system, is minimized so that less allyl glycidyl ether (II) need be used.

The process is conducted without a carboxamide, which facilitates the obtention of pure hydrosilylation product.

Various other objects, features and attendant advantages of the present invention will be more fully appreciated as the same becomes better understood from the following detailed description.

DETAILED DESCRIPTION OF THE INVENTION

The alkyl radicals in the trialkoxysilanes (III), and hence also in the 3-glycidyloxypropyltrialkoxysilanes (1), are preferably alkyl radicals 1 to 4 carbon atoms. Methyl and ethyl radicals are particularly preferred. Like allyl glycidyl ether (II), trimethoxy- and triethoxysilane are obtainable commercially, or can be readily prepared by reacting trichlorosilane with methanol or ethanol according to well-known procedures.

Suitable starting materials for the Pt(0) portion of the supported catalyst are any desired platinum(II) or platinum (IV) compounds that are soluble preferably in water or else in other solvents, such as platinum(II) nitrate, platinum(IV) acetylacetonate, platinum(IV) chloride, platinum(IV) acetate, hexachloroplatinic(IV) acid and its complexes, for example with sym-divinyl-tetramethyidisiloxane. Examples of suitable supports are active carbon, alumina, precipitated or pyrogenic silica, silicates, magnesium oxide, and natural or synthetic zeolites. Preference is given to supports with a large surface area, so that the finished catalyst has a specific surface area of from 10 to 400 m$^2$/g as measured by the method of Brunauer, Emmett and Teller (BET method; P. W. Atkins, Physical Chemistry, 4th Edition, p 779 ff., Oxford University Press (1986) incorporated herein by reference) with N$_2$ adsorption.

For the preparation, the support is impregnated or sprayed with a preferably aqueous solution, generally with a strength of from 0.1 to 10 percent by mass, of the platinum(II) or platinum(IV) compound. The amount and/or concentration of the solution are advantageously such that the platinum(0) content of the finished catalyst is from 0.01 to 1 percent by mass, advantageously from 0.02 to 0.2 percent by mass. Larger proportions of platinum, although doing no harm, bring no proportionate advantage either. Following the impregnation, the catalyst precursor is dried with the platinum compound, drying taking place, for example, in a stream of air at 80° C., and by passing hydrogen over the dried catalyst precursor at from 80 to 140° C. the platinum compound is reduced to elemental platinum(0), so producing the catalyst. The reduction is advantageously conducted at the site of the hydrosilylation reaction. In other words, in the same reactor used for the hydrosilation.

The hydrosilylation reaction is advantageously conducted without the concomitant use of an inert solvent and at temperatures from 20 to 200° C., in particular from 60 to 160° C. At lower temperatures the reaction rate is too low for a practicable process; at higher temperatures, byproducts are formed to a considerable extent. The process can be carried out under atmospheric pressure (1 bar abs.). Alternatively, and especially in the case of finely divided supports, the flow traversal of the catalyst zone can be promoted by applying a superatmospheric pressure, of up to 20 bar abs., for example. The residence time at the temperatures stated is generally from 1 to 100 minutes, in particular from 10 to 30 minutes. The molar ratio of the starting materials (II) and (III) can vary within wide limits and is generally in the range from 0.1 to 10, in particular from 0.25 to 4.

The hydrosilylation of the invention is judiciously carried out on a fixed catalyst (fixed bed). Examples of suitable reactors are a tubular reactor with or without circulation, a tube-bundle reactor, a tray reactor or a crossflow reactor. The process can be carried out continuously, for example, by arranging the catalyst in a vertical tubular reactor and allowing the starting materials, in each case alone or as a mixture, to trickle over the catalyst, which is maintained at the reaction temperature by means of external heating. In a batchwise variant of the process the reaction mixture, after it is passed through the fixed bed of catalyst, is guided via an external circuit back to the catalyst and trickled over the fixed bed again. This procedure is repeated until the desired degree of conversion has been reached. The total residence time is thus broken down into a number of sublimes corresponding to the number of circulations. Irrespective of the nature of the reaction regime, the reaction mixture is always broken down into its constituents by means of continuous or batchwise distillation.

By proceeding in accordance with the invention the glycidyloxypropyltrialkoxysilanes (I) are obtained in conversions of up to 100% with space-time yields of up to 1,000 mol/(h·g$_{Pt}$) and selectivities of up to 95%.

Having generally described this invention, a further understanding can be obtained by reference to certain specific examples which are provided herein for purposes of illustration only and are not intended to be limiting unless otherwise specified.

EXAMPLES

Example 1

A batchwise-operated tubular reactor with an external circuit which contains the catalyst bed is used to react the starting materials allyl glycidyl ether (II) (AGE) and trimethoxysilane (III) (TMOS) to 3-glycidyloxypropyltrimethoxysilane (I) (GLYMO); a circulation pump ensures that the catalyst bed is traversed from top to bottom by the flow. The catalyst employed comprises 11.2 g of active carbon with 0.1% by mass platinum, prepared by impregnating the active carbon with a 5 percent strength by mass aqueous solution of platinum(II) nitrate and reducing the platinum(II) compound in a stream of hydrogen (8 h at 100° C.), and, as starting material, a mixture of 342 g of trimethoxysilane (III) (2.8 mol) and 348 g of allyl glycidyl ether (II) (3.05 mol). The reaction is conducted isothermally at 120° C., with the duration of catalyst contact being 3 s on each circulation. After 75 minutes, 3-glycidyloxypropyltrimethoxysilane (I) has been formed with a selectivity of 92.2%. The table below indicates the composition of the reaction mixture, as determined by gas chromatography, after the end of the reaction:

| Substance | Amount (g) |
| --- | --- |
| Trimethoxysilane (III) | 49.0 |
| Allyl glycidyl ether (II) | 12.2 |
| 3-Glycidyloxypropyltrimethoxysilane (I) | 522.3 |
| 1-Methylvinyl glycidyl ether | 80.45 |
| iso-3-Glycidyloxypropyltrimethoxysilane (IV) | 8.25 |
| Tetramethoxysilane | 17.8 |

No high-boiling components are formed, nor is any heterocyclic compound (V) produced. The space-time yield is 158 mol of GLYMO/(h·$g_{Pt}$).

Example 2

A continuously operated fixed bed reactor without an external circuit and having a volume of 170 cm³ is used to react allyl glycidyl ether (II) (AGE) and trimethoxysilane (III) (TMOS) to 3-glycidyloxypropyltrimethoxysilane (I) (GLYMO) at 120° C. and under a pressure of 3 bar. The fixed bed reactor is filled with a catalyst comprising 70 g of active carbon with 0.02% by mass of platinum, prepared in the same way as the catalyst of Example 1. The fixed bed reactor is charged with 2.326 mol/h trimethoxysilane (TMOS) and 2.561 mol/h allyl glycidyl ether (AGE). The molar ratio of AGE to TMOS is therefore 1.1:1. The starting materials were supplied in liquid phase by way of metering pumps. The table below indicates the composition of the reaction mixture (initial flow) as determined by gas chromatography:

| Substance | Amount (g) |
| --- | --- |
| Trimethoxysilane (III) | 28.4 |
| Allyl glycidyl ether (II) | 8.5 |
| 3-Glycidyloxypropyltrimethoxysilane (I) | 454.7 |
| 1-Methylvinyl glycidyl ether | 59.8 |
| iso-3-Glycidyloxypropyltrimethoxysilane (IV) | 9.1 |
| Tetramethoxysilane | 19.3 |

The conversion of the trimethoxysilane is 90%, the selectivity for the desired GLYMO (I) 91.9%. The selectivity for iso-GLYMO is 1.83%, that for tetramethoxysilane 6.05%. No high-boiling components are formed, nor is any heterocyclic isomeric GLYMO (V) produced. The residence time on the catalyst is 16.8 minutes, the space-time yield of GLYMO 137.4 mol/(h·$g_{PT}$). The reaction mixture is worked up either by batchwise or continuous distillation, with unreacted TMOS and AGE being recycled to the reactor.

Obviously, numerous modifications and variations of the present invention are possible in light of the above teachings. It is therefore to be understood that within the scope of the appended claims, the invention may be practiced otherwise than as specifically described herein.

German Patent Application No. 198 050 83.6, filed Feb. 9, 1998, is incorporated herein by reference in its entirety.

What is claimed is:

1. A process for preparing a 3-glycidyloxypropyltrialkoxysilane represented by the formula (I):

$$CH_2(O)CHCH_2—O—(CH_2)_3Si(OR)_3 \qquad (I),$$

wherein R is an alkyl radical,
comprising:
heterogeneously catalyzing the reaction of an allyl glycidyl ether represented by formula (II):

$$CH_2(O)CHCH_2—O—CH_2CH=CH_2 \qquad (II),$$

and a trialkoxysilane represented by formula (III):

$$HSi(OR)_3 \qquad (III),$$

with a platinum(0) catalyst on a nonmetallic support.

2. The process of claim 1, wherein R has 1 to 4 carbon atoms.

3. The process of claim 1, wherein R is methyl or ethyl.

4. The process of claim 1, wherein the molar ratio of allyl glycidyl ether (II) to trialkoxysilane (III) is 0.1 to 10.

5. The process of claim 4, wherein said molar ratio is 0.25 to 4.

6. The process of claim 1, wherein the proportion of platinum in the catalyst by mass is 0.01 to 1.0%, the support comprises active carbon, alumina or silica, and the specific surface area of the catalyst is 10 to 400 m²/g.

7. The process of claim 1, wherein the proportion of platinum in the catalyst by mass is 0.02 to 0.1%.

8. The process of claim 1, wherein the catalyst is free from halide.

9. The process of claim 1, wherein the reaction is conducted at a temperature of 20 to 200° C. and under a pressure of from 1 to 20 bar abs.

10. The process as claimed in claim 9, wherein the reaction is conducted at a temperature of 60 to 160° C.

11. The process of claim 1, wherein the reaction is conducted on a fixed bed of catalyst in a tubular reactor, with or without circulation, in a tube-bundle reactor, in a tray reactor or in a crossflow reactor.

12. The process of claim 1, wherein the yield of (I) is 90 to 100%.

13. The process of claim 1, wherein the nonmetallic support comprises active carbon, alumina, silica, silicates, magnesium oxide or zeolites.

14. The process of claim 1, wherein R has 1 to 4 carbon atoms.

15. The process of claim 14, wherein the reaction is conducted at a temperature of 20 to 200° C.

16. The process of claim 15, wherein the nonmetallic support comprises active carbon, alumina, silica, silicates, magnesium oxide or zeolites.

17. The process of claim 16, wherein the molar ratio of allyl glycidyl ether (II) to trialkoxysilane (III) is 0.1 to 10.

18. The process of claim 17, wherein the yield of (I) is 90 to 100%.

* * * * *